US006824599B2

(12) United States Patent
Swatloski et al.

(10) Patent No.: US 6,824,599 B2
(45) Date of Patent: Nov. 30, 2004

(54) DISSOLUTION AND PROCESSING OF CELLULOSE USING IONIC LIQUIDS

(75) Inventors: Richard Patrick Swatloski, Tuscaloosa, AL (US); Robin Don Rogers, Tuscaloosa, AL (US); John David Holbrey, Tucaloosa, AL (US)

(73) Assignee: The University of Alabama, Tuscaloosa, AL (US)

( * ) Notice: Subject to any disclaimer, the term of this patent is extended or adjusted under 35 U.S.C. 154(b) by 0 days.

(21) Appl. No.: 10/256,521

(22) Filed: Sep. 27, 2002

(65) Prior Publication Data

US 2003/0157351 A1 Aug. 21, 2003

Related U.S. Application Data

(60) Provisional application No. 60/326,704, filed on Oct. 3, 2001.

(51) Int. Cl.$^7$ .............................. C08L 1/00; C08L 1/02; D01F 2/02
(52) U.S. Cl. .............................. 106/163.01; 106/200.2; 106/164.3
(58) Field of Search .......................... 106/164.3, 200.2, 106/163.01

(56) References Cited

U.S. PATENT DOCUMENTS

| | | | |
|---|---|---|---|
| 1,943,176 A | | 1/1934 | Graenacher |
| 5,679,146 A | * | 10/1997 | Kalt et al. ............. 106/166.01 |
| 5,683,832 A | | 11/1997 | Bonhote et al. |
| 5,827,602 A | | 10/1998 | Koch et al. |

OTHER PUBLICATIONS

Bonhôte et al., "Hydrophobic, Highly Conductive Ambient-Temperature Molten Salts", *Inorg. Chem.*(1996), no month provided, 35:1168–1178.
Fannin et al., "Properties of 1,3-Dialkylimidazollum Chloride–Aluminum Chloride Ionic Liquids. 2. Phase Transitions, Densities, Electrical Conductivities, and Viscosities", *J. Phys. Chem.* (1984), no month provided, 88:2614–2621.
Fisher et al., "Structural Changes of Cellulose Dissolved in Molten Salt Hydrates", Book of Abstracts, 219th ACS national meeting, San Francisco, California,(Mar. 26–30, 2000)(Abstract Only).
Holbrey et al., "The Phase Behaviour of 1-Alkyl-3-Methlimidazolium Tetrafluoroborates; Ionic Liquids and Ionic Liquid Crystals", *J. Chem. Soc., Dalton Trans.* (1999), no month provided, 2133–2139.

Husemann et al., "Homogeneous Acetylation of Cellulose", *Buletinul Institutului Politehnic din Iasi* (1970), no month provided, 16(1):47–51 (Abstract Only).
Leipner et al., "Structural Changes of Cellulose Dissolved in Molten Salt Hydrates", *Macromol. Chem. Phys.*, (2000), no month provided, 201(15):2041–2049.
Maia et al., "Cellulose Organic Solvents. I. The Structures of Anhydrous N–Methylmorpholine N–Oxide and N–Methylmorpholine N–Oxide Monohydrate", *Acta. Cryst.*, (1981), no month provided, B37:1858–1862.
Marson et al., "A Novel, Efficient Procedure for Acylation of Cellulose Under Homogeneous Solution Conditions", *J. of Applied Polymer Science* (1999), no month provided, 74: 1355–1360.
Ngo et al., "Thermal Properties of Imidazolium Ionic Liquids", *Thermochimica. Acta 357–358* (2000), no month provided, 97–102.
Shriver et al., *Inorganic Chemistry*, W.H. Freeman & Co., New York (1990), no month provided, 406–407.
Suarez et al., "Synthesis and Physical–Chemical Properties of Ionic Liquides Based on 1–n–butyl–3–methylimidazolium Cation", *J. Chim. Phys.* (1998), no month provided, 95:1626–1639.
Wilkes et al., "Air and Water Stable 1–Ethyl–3–methylimidazolium Based Ionic Liquids", *J. Chem. Soc., Chem. Commun.* (1992), no month provided, 965–967.
Okamoto and Shimakawa,(1970), no month provided, *J. Org. Chem.*, 35(11):3752–3756.
Heinze et al.,(2001), no month provided, *Prog. Polym. Sci.*, 26:1689–1762.
Swatloski et al.(2002), no month provided, *J. Am. Chem. Soc.*124:4974–4975.
Swatloski et al.,(2002), no month provided, "Ionic Liquids for the dissolution and regeneration of cellulose"; In *Molten Salts XIII, Proceedings of the thirteenth international symposium on molten salts*; De Long et al. eds. 2002, pp. 155–165.

* cited by examiner

Primary Examiner—David Brunsman
(74) Attorney, Agent, or Firm—Welsh & Katz, Ltd.

(57) ABSTRACT

Cellulose is dissolved in an ionic liquid without derivatization, and is regenerated in a range of structural forms without requiring the use of harmful or volatile organic solvents. Cellulose solubility and the solution properties can be controlled by the selection of the ionic liquid constituents, with small cations and halide or pseudohalide anions favoring solution.

58 Claims, 3 Drawing Sheets

DISSOLUTION AND PROCESSING OF CELLULOSE USING IONIC LIQUIDS

This application claims benefit of U.S. Provisional 60/326,704 filed Oct. 3, 2001.

BACKGROUND ART

Cellulose is the most abundant biorenewable material and cellulose-derived products have been used in all cultures from the most primitive to highly developed modern technological society. Apart from the use of unmodified cellulose-containing materials (for example wood, cotton), modern cellulose technology requires extraction and processing of cellulose from primary sources using techniques that have changed very little since the inception of the modern chemical industry.

Cellulose and its derivatives can be substituted as a source for a number of chemicals. For example, petroleum feed stocks can be substituted with cellulose to prepare polymers for applications in paints, plastics and other formulation materials. Cellophane is prepared through the intermediacy of viscose that is dissolved, and then regenerated, whereas chemical dissolution typically incorporating derivatization such as ester or ether formation yields a wide range of modern materials.

The primary chemistry for transformation of cellulose is esterification; cellulose esters have important large-scale applications in the paper industry, for the preparation of fibers and textiles, as well as polymers and films. Mixed esters such as acetate/propionate or acetate/butyrate are used in plastics. Mixed esters are also used as rheological modifiers, for example in automotive paints to permit metal flakes to orient, which improves finish and drying times. Microcrystalline cellulose is also marketed as a dietary food additive and in pharmaceutical preparations.

The full potential of cellulose and cellulose products has not been fully exploited, partially due to the historical shift towards petroleum-based polymers from the 1940's onwards, and also by the limited number of common solvents in which cellulose is readily soluble. Traditional cellulose dissolution processes, including the cuprammonium and xanthate processes, are often cumbersome or expensive and require the use of unusual solvents, typically with a high ionic strength and are used under relatively harsh conditions. [Kirk-Othmer "Encyclopedia of Chemical Technology", Fourth Edition 1993, volume 5, p. 476–563.] Such solvents include carbon disulfide, N-methylmorpholine-N-oxide (NMMO), mixtures of N,N-dimethylacetamide and lithium chloride (DMAC/LiCl), dimethylimidazolone/LiCl, concentrated aqueous inorganic salt solutions [$ZnCl/H_2O$, $Ca(SCN)_2/H_2O$], concentrated mineral acids ($H_2SO_4/H_3PO_4$) or molten salt hydrates ($LiClO_4.3H_2O$, $NaSCN/KSCN/LiSCN/H_2O$).

Physical and chemical processing methods for treating cellulosic resources are numerous. Chemical, enzymic, microbiological and macrobiological catalysts can be used to accelerate the process under conditions selected to be thermodynamically favorable to product formation. Chemical processes include oxidation, reduction, pyrolysis, hydrolysis, isomerization, esterification, alkoxylation and copolymerization. Chemical and enzymatic hydrolysis of cellulose is discussed in 'The Encyclopedia of Polymer Science and Technology', 2nd Ed, J. I. Kroschwitz (Ed in Chief), Wiley (New York), 1985. Wood, paper, cotton, rayon, cellulose acetate, and other textiles are a few examples of the broad range of cellulosic materials.

With increasing industrial pollution and consequent governmental regulations, the need to implement 'green' processes to prevent pollution and waste production and to utilize renewable resources is becoming increasingly prominent. The efficiency of existing methods for dissolving and derivatizing cellulose can be significantly improved by the availability of suitable solvents for refined and natural cellulose; an example is N-methylmorpholine-N-oxide (NMMO), used as a solvent for non-derivatizing dissolution of cellulose for the production of lyocell fibers. [http://www.lenzing.com.]

The use of ionic liquids as replacements for conventional organic solvents in chemical, biochemical and separation processes has been demonstrated. Graenacher first suggested a process for the preparation of cellulose solutions by heating cellulose in a liquid N-alkylpyridinium or N-arylpyridinium chloride salt, U.S. Pat. No. 1,943,176, especially in the presence of a nitrogen-containing base such as pyridine. However, that finding seems to have been treated as a novelty of little practical value because the molten salt system was, at the time, somewhat esoteric. This original work was undertaken at a time when ionic liquids were essentially unknown and the application and value of ionic liquids as a class of solvents had not been realized.

It has now been found that cellulose can be dissolved in solvents that are now described as ionic liquids that are substantially free of water, nitrogen-containing bases and other solvents. It has also been found that a wide and varied range of ionic liquids can be used to provide a greater control and flexibility in the overall processing methodology. It has further been found that cellulose-containing materials can be obtained from an ionic liquid solvent system without using volatile organic or other undesirable solvents in the process. These findings are discussed in the disclosure that follows.

BRIEF SUMMARY OF THE INVENTION

A method for dissolving cellulose is contemplated. That method comprises admixing cellulose with a hydrophilic ionic liquid comprised of cations and anions in the substantial absence of water or a nitrogen-containing base to form an admixture. The admixture is agitated until dissolution is complete. The admixture is heated in some embodiments, and that heating is preferably carried out by microwave irradiation. The ionic liquid is molten at a temperature less than about 150° C.

The cations of an ionic liquid are preferably cyclic and correspond in structure to a formula selected from the group consisting of

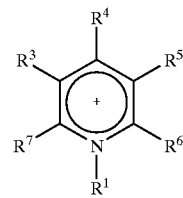

PYRIDINIUM

PYRIDAZINIUM

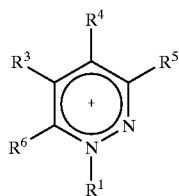

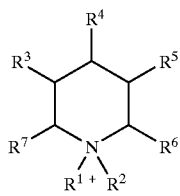

PIPERIDINIUM

PYRIMIDINIUM

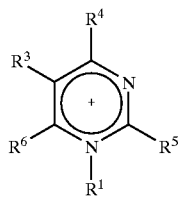

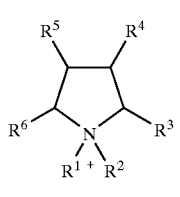

PYRROLIDINIUM

PYRAZINIUM

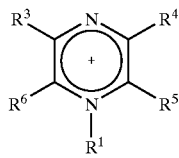

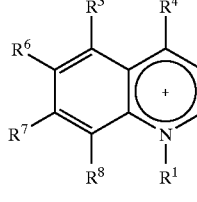

and

QUINOLINIUM

IMIDAZOLIUM

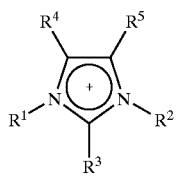

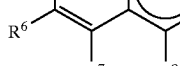

ISOQUINOLINIUM

PYRAZOLIUM

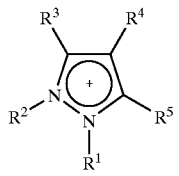

OXAZOLIUM

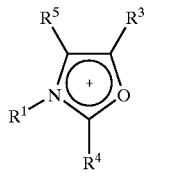

wherein $R^1$ and $R^2$ are independently a $C_1$–$C_6$ alkyl group or a $C_1$–$C_6$ alkoxyalkyl group, and $R^3$, $R^4$, $R^5$, $R^6$, $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group. The anions of the ionic liquid are halogen, pseudohalogen, or $C_1$–$C_6$ carboxylate. It is to be noted that there are two iosmeric 1,2,3-triazoles. It is preferred that all R groups not required for cation formation be hydrido.

A cation that contains a single five-membered ring that is free of fusion to other ring structures is more preferred. A cellulose dissolution method is also contemplated using an ionic liquid comprised of those cations. That method comprises admixing cellulose with a hydrophilic ionic liquid comprised of those five-membered ring cations and anions in the substantial absence of water to form an admixture. The admixture is agitated until dissolution is complete. Exemplary cations are illustrated below wherein $R^1$, $R^2$, and $R^3$–$R^5$, when present, are as defined before.

1, 2, 3-TRIAZOLIUM

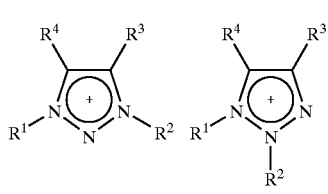

1, 2, 3-TRIAZOLIUM

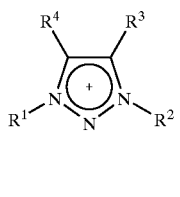

1, 2, 4-TRIAZOLIUM

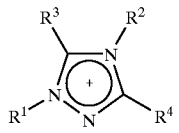

1, 2, 4-TRIAZOLIUM

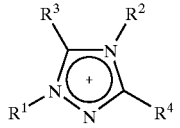

THIAZOLIUM

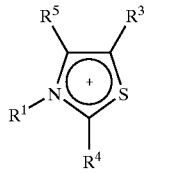

-continued

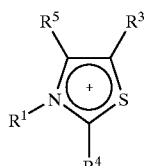
THIAZOLIUM

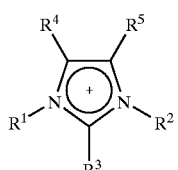
IMIDAZOLIUM

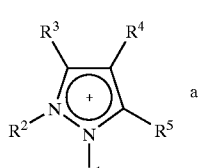
PYRAZOLIUM and

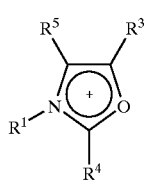
OXAZOLIUM

Of the more preferred cations that contain a single five-membered ring free of fusion to other ring structures, an imidazolium cation that corresponds in structure to Formula A is particularly preferred, wherein $R^1$, $R^2$, and $R^3$–$R^5$, are as defined before.

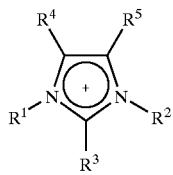

A

A 1,3-di-($C_1$–$C_6$ alkyl)-substituted-imidazolium ion is a more particularly preferred cation; i.e., an imidazolium cation wherein $R^3$–$R^5$ of Formula A are each hydrido, and $R^1$ and $R^2$ are independently each a $C_1$–$C_6$-alkyl group or a $C_1$–$C_6$ alkoxyalkyl group. A 1-($C_1$–$C_6$-alkyl)-3-(methyl)-imidazolium [$C_n$-mim, where n=1–6] cation is most preferred, and a halogen is a preferred anion. A most preferred cation is illustrated by a compound that corresponds in structure to Formula B, below, wherein $R^3$–$R^5$ of Formula A are each hydrido and $R^1$ is a $C_1$–$C_6$-alkyl group or a $C_1$–$C_6$ alkoxyalkyl group.

B

A solution comprised of cellulose in a molten hydrophilic ionic liquid solvent that is substantially free of water or a nitrogen-containing base is also contemplated. As above, the ionic liquid is comprised of cations and anions that are preferably those discussed above. A more preferred solution is comprised of cellulose dissolved in a hydrophilic liquid whose cations contain a single five-membered ring free of fusion to other ring structures, as discussed previously. A contemplated solution can be used as is to carry out further reactions on the cellulose such as acylation to form cellulose acetate or butyrate, or for regeneration.

A method for regenerating cellulose is also contemplated. That method comprises admixing a solution of cellulose in a molten hydrophilic ionic liquid solvent that is substantially free of water or nitrogen-containing base, or in a hydrophilic ionic liquid whose cations contain a single five-membered ring free of fusion to other ring structures with a liquid non-solvent for the cellulose that is miscible with the ionic liquid. The admixing causes the cellulose and ionic liquid to form solid and liquid phases, respectively. The solid phase is the regenerated cellulose that is preferably collected, as compared to being further reacted in situ. The ionic liquids used in this method are those discussed above.

BRIEF DESCRIPTION OF THE DRAWINGS

In the drawings forming a portion of this disclosure.

DETAILED DESCRIPTION OF THE INVENTION

Figure 1:
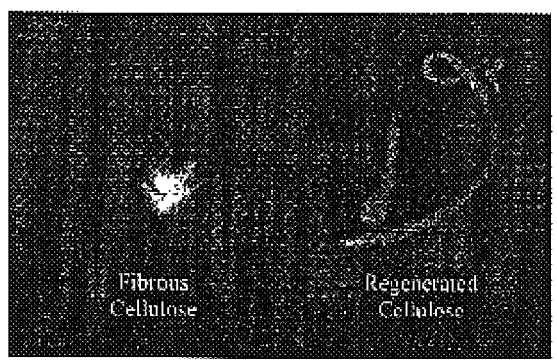
FIG. 1 shows two photographs of original fibrous cellulose (left) and regenerated cellulose (right) prepared by extrusion from a wide-bore syringe into water, illustrating that monolithic forms can be readily prepared.

The present invention relates to the formation of cellulose solutions in hydrophilic ionic liquids. The solvent is a hydrophilic ionic liquid, comprising an organic cation and an inorganic or organic anion.

A method for dissolving cellulose is contemplated as one embodiment of the invention. In one aspect, that method comprises admixing cellulose with a hydrophilic ionic liquid comprised of cations and anions in the substantial absence of water or a nitrogen-containing base to form an admixture. The admixture is agitated until dissolution is complete. The admixture is heated in some embodiments, and that heating is preferably carried out by microwave irradiation. The ionic liquid is molten at a temperature of less than about 150° C.

An exemplary cyclic ionic liquid cation corresponds in structure to a formula shown below,

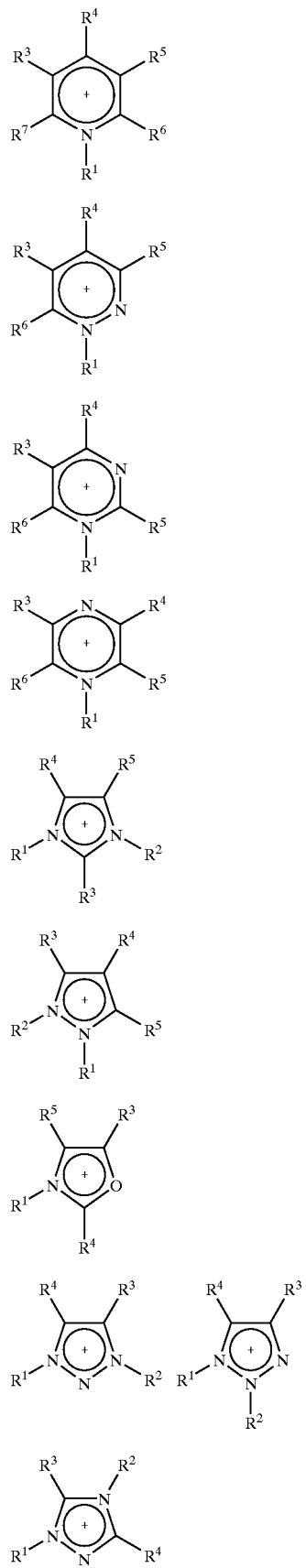
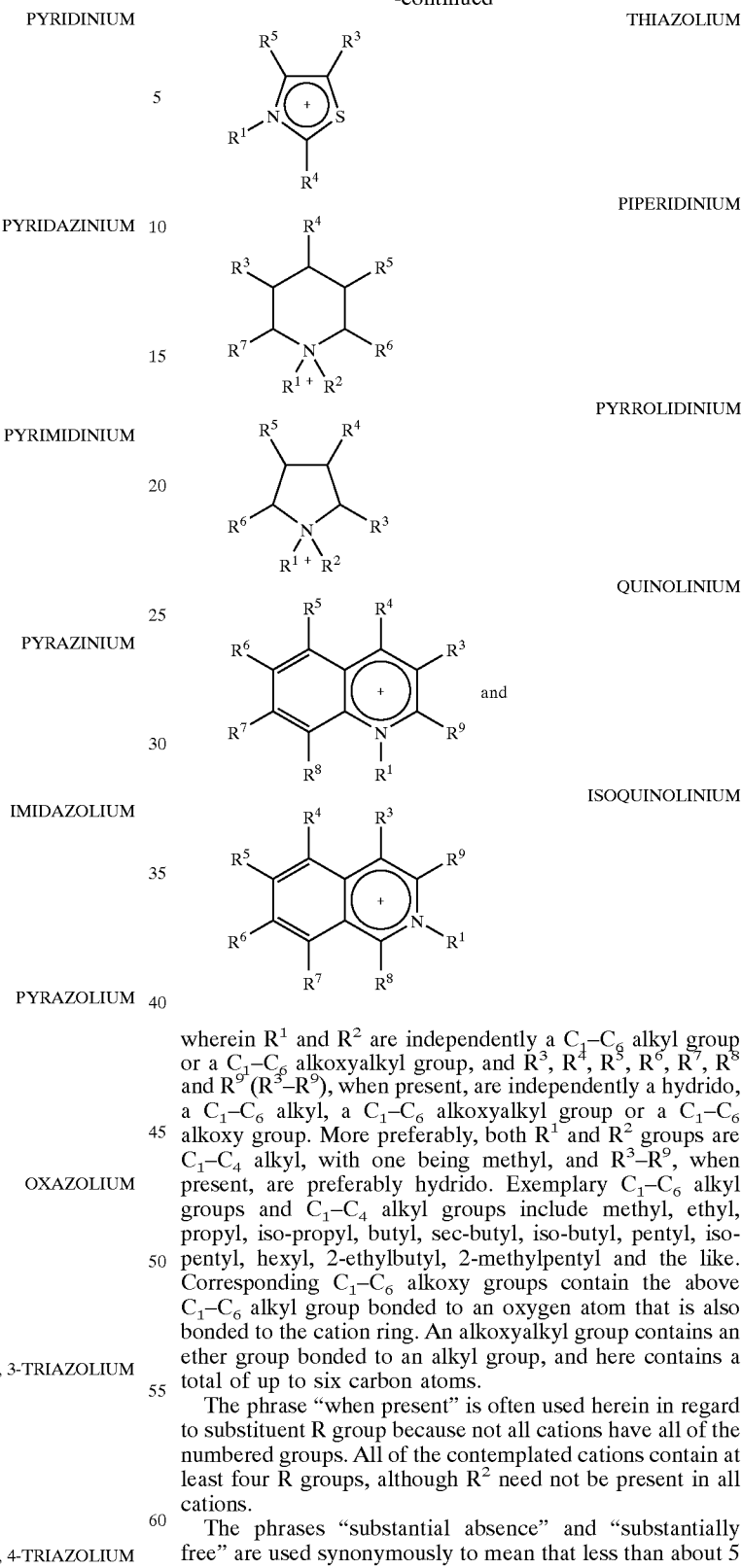

wherein $R^1$ and $R^2$ are independently a $C_1$–$C_6$ alkyl group or a $C_1$–$C_6$ alkoxyalkyl group, and $R^3$, $R^4$, $R^5$, $R^6$, $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group. More preferably, both $R^1$ and $R^2$ groups are $C_1$–$C_4$ alkyl, with one being methyl, and $R^3$–$R^9$, when present, are preferably hydrido. Exemplary $C_1$–$C_6$ alkyl groups and $C_1$–$C_4$ alkyl groups include methyl, ethyl, propyl, iso-propyl, butyl, sec-butyl, iso-butyl, pentyl, iso-pentyl, hexyl, 2-ethylbutyl, 2-methylpentyl and the like. Corresponding $C_1$–$C_6$ alkoxy groups contain the above $C_1$–$C_6$ alkyl group bonded to an oxygen atom that is also bonded to the cation ring. An alkoxyalkyl group contains an ether group bonded to an alkyl group, and here contains a total of up to six carbon atoms.

The phrase "when present" is often used herein in regard to substituent R group because not all cations have all of the numbered groups. All of the contemplated cations contain at least four R groups, although $R^2$ need not be present in all cations.

The phrases "substantial absence" and "substantially free" are used synonymously to mean that less than about 5 weight percent water is present, for example. More preferably, less than about one percent water is present in the composition. The same meaning is intended regarding the presence of a nitrogen-containing base.

An anion for a contemplated ionic liquid cation is preferably a halogen ion (chloride, bromide, or iodide), perchlorate, a pseudohalogen ion such as thiocyanate and cyanate or $C_1$–$C_6$ carboxylate. Pseudohalides are monovalent and have properties similar to those of halides [Schriver et al., *Inorganic Chemistry*, W. H. Freeman & Co., New York (1990) 406–407]. Pseudohalides include the cyanide ($CN^{-1}$), thiocyanate ($SCN^{-1}$), cyanate ($OCN^{-1}$), fulminate ($CNO^{-1}$) and azide ($N_3^{-1}$) anions. Carboxylate anions that contain 1–6 carbon atoms ($C_1$–$C_6$ carboxylate) and are illustrated by formate, acetate, propionate, butyrate, hexanoate, maleate, fumarate, oxalate, lactate, pyruvate and the like. A contemplated ionic liquid is hydrophilic and therefore differs from the hydrophobic ionic liquids described in Koch et al. U.S. Pat. No. 5,827,602 or those of Bonhôte et al. U.S. Pat. No. 5,683,832 that contain one or more fluorine atoms covalently bonded to a carbon atom as in a trifluoromethanesulfonate or trifluoroacetate anion.

It is preferred that all R groups that are not required for cation formation; i.e., those other than $R^1$ and $R^2$ for compounds other than the imidazolium, pyrazolium and triazolium cations shown above, be hydrido. Thus, the cations shown above preferably have a structure that corresponds to a structure shown below, wherein $R^1$ and $R^2$ are as described before.

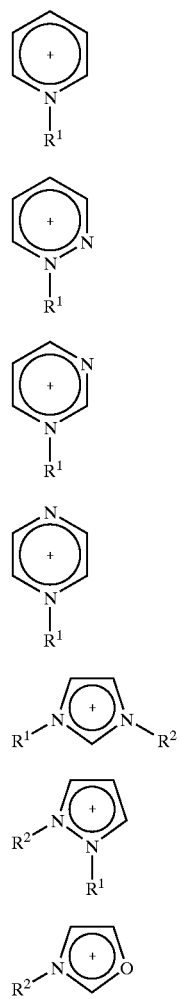

PYRIDINIUM

PYRIDAZINIUM

PYRIMIDINIUM

PYRAZINIUM

IMIDAZOLIUM

PYRAZOLIUM

OXAZOLIUM

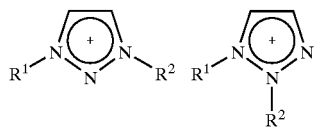

1,2,3-TRIAZOLIUM

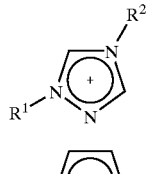

1,2,4-TRIAZOLIUM

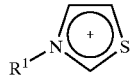

THIAZOLIUM

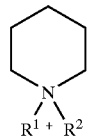

PIPERIDINIUM

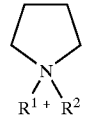

PYRROLIDINIUM

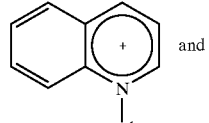

QUINOLINIUM and

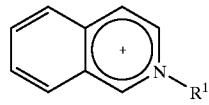

ISOQUINOLINIUM

A cation that contains a single five-membered ring that is free of fusion to other ring structures is more preferred. Exemplary cations are illustrated below wherein $R^1$, $R^2$, and $R^3$–$R^5$, when present, are as defined before.

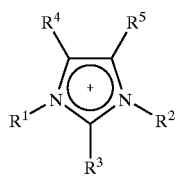

IMIDAZOLIUM

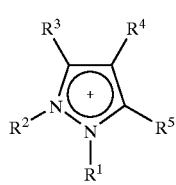

PYRAZOLIUM

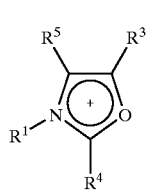

OXAZOLIUM

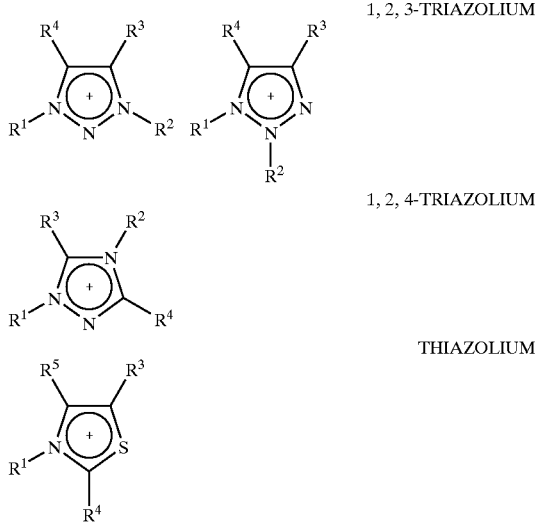

Another aspect of the invention contemplates a method for dissolving cellulose that comprises the steps of admixing cellulose with a molten ionic liquid in the substantial absence of water, to form an admixture. Here the ionic liquid is comprised of cations that contain a single five-membered ring that is free of fusion to other ring structures and anions. The resulting admixture is agitated until dissolution is complete. The admixture can be heated as discussed elsewhere herein to assist the dissolution.

Of the more preferred cations that contain a single five-membered ring free of fusion to other ring structures, an imidazolium cation that corresponds in structure to Formula A is particularly preferred, wherein $R^1-R^5$ are as defined before, and the anion of the ionic liquid is a halogen or pseudohalogen.

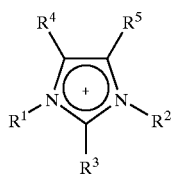

A 1,3-di-($C_1-C_6$ alkyl or $C_1-C_6$ alkoxyalkyl)-substituted-imidazolium ion is a more particularly preferred cation; i.e., an imidazolium cation wherein $R^3-R^5$ of Formula A are each hydrido, and $R^1$ and $R^2$ are independently each a $C_1-C_6$ alkyl or a group or $C_1-C_6$ alkoxyalkyl. More preferably still, one of the 1,3-di-$C_1-C_6$ alkyl groups ($R^1$ or $R^2$) is methyl. An anion of the ionic liquid whose cation corresponds in structure to a cation of Formula A is a halogen or pseudohalogen.

A 1-($C_1-C_6$-alkyl)-3-(methyl)-imidazolium [$C_n$-mim, where n=1–6] cation is most preferred, and a halogen is a most preferred anion. A most preferred cation is illustrated by a compound that corresponds in structure to Formula B, below, wherein $R^3-R^5$ of Formula A are each hydrido and $R^1$ is a $C_1-C_6$-alkyl group. A most preferred anion is a chloride ion.

A contemplated ionic liquid is liquid at or below a temperature of about 200° C., and preferably below a temperature of about 150° C. and above a temperature of about –100° C. For example, N-alkylisoquinolinium and N-alkylquinolinium halide salts have melting points of less than about 150° C. The melting point of N-methylisoquinolinium chloride is 183° C., and N-ethylquinolinium iodide has a melting point of 158° C. More preferably, a contemplated ionic liquid is liquid (molten) at or below a temperature of about 120° C. and above a temperature of minus 44° C. (–44° C.). Most preferably, a contemplated ionic liquid is liquid (molten) at a temperature of about –10° to about 100° C.

Cellulose can be dissolved without derivitization in high concentration in ionic liquids by heating to about 100° C., by heating to about 80° C. in an ultrasonic bath, and most effectively by using microwave heating of the samples using a domestic microwave oven. Using a microwave heater, it is preferred to heat the admixture of hydrophilic ionic liquid and cellulose to a temperature of about 100° to about 150° C.

A contemplated ionic liquid has an extremely low vapor pressure and typically decomposes prior to boiling. Exemplary liquification temperatures [i.e., melting points (MP) and glass transition temperatures (Tg)] and decomposition temperatures for illustrative 1,3-di-$C_1-C_6$-alkyl imidazolium ion-containing ionic liquids wherein one of $R^1$ and $R^2$ is methyl are shown in the table below.

| Ionic Liquid | Liquification Temperature (° C.) | Decomposition Temperature (° C.) | Citation* |
|---|---|---|---|
| [$C_2$mim]Cl | | 285 | a |
| [$C_3$mim]Cl | | 282 | a |
| [$C_4$mim]Cl | 41 | 254 | b |
| [$C_6$mim]Cl | −69 | 253 | |
| [$C_8$mim]Cl | −73 | 243 | |
| [$C_2$mim]I | | 303 | a |
| [$C_4$mim]I | −72 | 265 | b |
| [$C_4$mim][PF$_6$] | 10 | 349 | b |
| [$C_2$mim][PF$_6$] | 58–60 | 375 | c, a |
| [$C_3$mim][PF$_6$] | 40 | 335 | a |
| [iC$_3$mim][PF$_6$] | 102 | | a |
| [$C_6$mim][PF$_6$] | −61 | 417 | d |
| [$C_4$mim][BF$_4$] | −81 | 403, 360 | d, e |
| [$C_2$mim][BF$_4$] | | 412 | a |
| [$C_2$mim][C$_2$H$_3$O$_2$] | 45 | | c |
| [$C_2$mim][C$_2$F$_3$O$_2$] | 14 | About 150 | f | a Ngo et al., Thermochim. Acta, 2000, 357, 97.
b Fannin et al., J. Phys. Chem., 1984, 88, 2614.
c Wilkes et al., Chem. Commun., 1992, 965.
d Suarez et al., J. Chim. Phys., 1998, 95, 1626.
e Holbrey et al., J. Chem. Soc., Dalton Trans., 1999, 2133.
f Bonhôte et al., Inorg. Chem., 1996, 35, 1168.

Illustrative 1-alkyl-3-methyl-imidazolium ionic liquids, [$C_n$-mim]X [n=4 and 6, X=Cl⁻, Br⁻, SCN⁻, (PF$_6$)⁻, (BF$_4$)⁻] have been prepared, as has [$C_8$-mim]Cl whose use is not claimed. The dissolution of cellulose (fibrous cellulose, from Aldrich Chemical Co.) in those illustrative ionic liquids under ambient conditions and with heating to 100° C., with sonication and with microwave heating has been examined.

Dissolution is enhanced by the use of microwave heating. Cellulose solutions can be prepared very quickly, which is energy efficient and provides associated economic benefits.

A contemplated ionic liquid and a solution prepared from such a liquid is substantially free of water or a nitrogen-containing base to form an admixture. As such, such a liquid or solution contains about one percent or less water or a nitrogen-containing base. Thus, when a solution is prepared, it is prepared by admixing the ionic liquid and cellulose in the absence of water or a nitrogen-containing base to form an admixture.

The cellulose to be dissolved can be in substantially any form that is amenable to being wet by a liquid. Exemplary cellulose forms useful herein include cellulose as fibrous cellulose, wood pulp, linters, cotton balls and paper. For example, fibrous cellulose was dissolved at 25 weight percent in [$C_4$mim]Cl by microwave heating to provide an optically clear, viscous solution.

Cellulose can be dissolved in a range of ionic liquids. Cellulose can be dissolved for derivatization and for analysis, for example by size exclusion chromatography.

Cellulose can be readily dissolved in ionic liquids using a domestic microwave oven as a heating source. Microwave heating significantly enhances the dissolution of cellulose in ionic liquids. Microwave-induced dissolution of cellulose in ionic liquids is a very quick process so that decay of the degree of polymerization is reduced. Being a relatively fast process, dissolution is energy efficient.

Cellulose displays high solubility in the ionic liquids. Viscous, birefringent liquid crystalline solutions are obtained at high concentration, e.g. about 10 to about 25 weight percent.

A contemplated solution of cellulose in an ionic liquid can contain cellulose in an amount of about 5 to about 35 weight percent of the solution. More preferably, the cellulose is present at about 5 to about 25 weight percent of the solution. More preferably still, the cellulose is present at about 10 to about 25 weight percent of the solution.

Ionic liquids containing chloride anions appear to be most effective. The chloride anion is not required; reasonable solubility was also observed when the ionic liquid contained thiocyanate, perchlorate and bromide anions. No solubility was observed for ionic liquids containing tetrafluoroborate or hexafluorophosphate anions.

A range of different cations can be employed of those screened from the common sets used to prepare ionic liquids; imidazolium salts appeared to be most effective, with the smallest imidazolium cation exhibiting the easiest dissolution. Alkyl-pyridinium salts free of organic base were less effective and no significant solubility was observed in the long-chain alkylphosphonium chloride salt examined. Smaller phosphonium and ammonium quaternary salts containing shorter chain alkyl substituents are known, but have higher melting points and are often not liquid within the acceptable range for definition as ionic liquids.

The use of an imidazolium chloride ionic liquid as solvent for cellulose provides a significant improvement over the previously-reported solubility of cellulose in the organic salt/base N-benzylpyridinium chloride/pyridine as discussed in U.S. Pat. No. 1,943,176, and in which the maximum solubility was 5 weight percent. Indeed, additional nitrogen-containing bases as were used in that patent are not required to obtain good solubility of cellulose in the ionic liquids.

Cellulose can be regenerated by admixing (contacting) the ionic liquid solution with a liquid non-solvent for the cellulose that is miscible with the ionic liquid. The liquid non-solvent is preferably miscible with water. Exemplary liquid non-solvents include water, an alcohol such as methanol, or ethanol, acetonitrile, an ether such as furan or dioxane and a ketone such as acetone. The advantage of water is that the process avoids the use of a volatile organic compound (VOC). Regeneration does not require the use of volatile organic solvents. The ionic liquid can be dried and reused after regeneration.

Cellulose can be regenerated from the ionic liquids in a variety of structural forms. These can include flocs or powders (prepared by bulk quenching), tubes, fibers and extrudates, and films. During extrusion, the cellulose composite can be manipulated to prepare different forms. The regenerated cellulose appears to be relatively homogenous from scanning electron micrograph (SEM) pictures. In preparing tubes, fibers and other extrudates, the admixing step is carried out by extruding the cellulose solution through a die and into the non-solvent.

EXAMPLE 1

Cellulose Dissolution

It was found that the best ionic liquid for dissolution of an illustrative test material, regenerated fibrous cellulose, was [$C_4$mim]Cl. In a generic procedure, fibrous cellulose (0.2 g) was placed in molten [$C_4$mim]Cl (2 g) in a glass vial and heated in a domestic microwave oven with 3×5 seconds heating pulses. After each heating pulse, the vial was removed and vortexed to mix the contents, then replaced in the microwave. A viscous, optically clear solution of cellulose in the ionic liquid was obtained.

Solutions could be prepared in this manner with varying concentrations of cellulose dissolved in the ionic liquid. The solutions were increasingly viscous with cellulose concentration. At 25 weight percent of cellulose, the clear solution is still workable. At higher cellulose concentrations, an opaque viscous gel was formed. The effective solubility limit for cellulose in [$C_4$mim]Cl was not clearly identified, but depends on the degree of mechanical processing of the highly viscous paste formed when the cellulose composition is over 25 weight percent.

The solubility of cellulose in [$C_4$mim]Cl is significantly higher than can be obtained using other solvents. For example solutions of cellulose dissolved to a maximum of 5 weight percent in molten inorganic salt hydrates have been described. [Leipner et al., *Macromol. Chem. Phys.*, (2000) 201:2041.]

Using conventional heating, dissolution of cellulose was slow, taking up to several hours heating at 70–100° C. to obtain a clear solution. By periodically placing the samples in an ultrasonic bath, the rate of dissolution was enhanced.

EXAMPLE 2

Cellulose Dissolution in 1,3-dialkylimidazolium Salts as a Function of Anions and Cations Cellulose was readily dissolved in the ionic liquids in high concentrations compared to usual solvents. Ionic liquids with different cations were screened as their chloride salts. These included [$C_6$mim]Cl and [$C_8$mim]Cl. The solubility of cellulose in the imidazolium-based ionic liquids was found to decrease with increasing alkyl-chain length on the cation.

A range of anions, varying from small, hydrogen-bond acceptors (Cl$^-$) to large, non-coordinating anions (tetrafluoroborate and hexafluorophosphate) were screened as [$C_4$mim]$^+$salts. The anions included Cl, Br, thiocyanate, perchlorate, hexafluorophosphate and tetrafluoroborate. These results are shown in Table 1, hereinafter.

It was found that ionic liquids containing anions that are strong hydrogen bond acceptors (halogen and pseudohalogen) gave good dissolution results. All these anions are known to be hydrogen-bond acceptors and to participate in extended hydrogen-bonding networks. It has also been determined that cellulose could not be dissolved in ionic liquids containing 'non coordinating' anions, including $BF_4^-$, and $PF_6^-$. Other non-coordinating anions include the trifluoromethylsulfonyl-containing anions such as trifluoromethylsulfonate, bis-trifluoromethylsulfonylamide ($NTf2^-$) and the like.

Thus, requirements for dissolution appear to include the presence of the strongly coordinating anion. The aromatic cation, which can participate in hydrogen-bond donation, may also be necessary, though these cations are weak H-bond donors.

The importance of hydrogen-bond properties of solvents for the dissolution of cellulose has been recognized. For example, NMMO can form two hydrogen bonds with water or polysaccharides. [Maia et al., *Acta. Cryst. B*, (1981) 37:1858.] Both anhydrous NMMO and the monohydrate are good solvents for cellulose. However, when hydrated with two or more waters, NMMO is no longer a solvent for cellulose, and is preferentially solvated by water.

Heating of the samples is usually required to enable dissolution. The effect of that heating may be to permit the ionic liquid solvent to penetrate into the fiber wall, which enables breaking of the fiber and microfibril structure and competitive hydrogen-bonding with encapsulated water.

Ionic liquids are very efficiently heated under microwave conditions. Thus, highly localized temperatures can be obtained that promote dissolution of cellulose by disrupting the strong, water mediated hydrogen-bonding of the natural polymer chains.

TABLE 1

Solubility of Fibrous Cellulose in Ionic Liquids

| Ionic Liquid | Method | Solubility (weight percent) |
| --- | --- | --- |
| [C$_4$mim]Cl | heat (100° C.) (70° C.) | 5 percent– 3 percent |
| [C$_4$mim]Cl | heat (80° C.) + sonication | 5 percent |
| [C$_4$mim]Cl | microwave heating (3 × 5 second pulses) | 25 percent, clear viscous solution |
| [C$_4$mim]Br | microwave | 5–7 percent |
| [C$_4$mim]SCN | microwave | 5–7 percent |
| [C$_4$mim][BF$_4$] | microwave | insoluble |
| [C$_4$mim][PF$_6$] | microwave | insoluble |
| PR$_4$Cl* | microwave | insoluble |
| NR$_4$Cl* | microwave | decomposed |
| [C$_6$mim]Cl | heat (100° C.) | 5 percent |
| [C$_8$mim]Cl | heat (100° C.) | sparingly sol |

*PR$_4$Cl = tetradecyl-trihexylphosphonium chloride;
NR$_4$Cl = tetrabutylammonium chloride.

EXAMPLE 3

Cellulose Regeneration

It was found that cellulose was precipitated from the ionic liquid solution by the addition of water. This incompatibility is the basis for the regeneration procedure described below.

The concentration of water that could be present in [C$_4$mim]Cl, while maintaining the solvent properties of the ionic liquid were measured by adding known amounts of water to the ionic liquid and then performing the dissolution process with microwave heating. When the water content of the ionic liquid was greater than about 1 weight percent (approximately 0.5 mole fraction $H_2O$), the solvent properties were significantly impaired and fibrous cellulose was found to be no longer soluble.

When high concentrations of cellulose (greater than 10 weight percent) were dissolved in the [C$_4$mim]Cl, solutions were obtained that were optically anisotropic between crossed polarizing filters and displayed birefringence. The formation of liquid crystalline solutions of cellulose can have useful applications for the generation of new, advanced materials. The conservation of anisotropy in the solid phase is especially desirable, leading to enhanced mechanical properties and high strength materials. In addition, in other areas such as optics, specific qualities due to the anisotropy can also be exploited.

EXAMPLE 4

Cellulose Solubility Studies

The solubility of cellulose in ionic liquids can be controlled by changes in the anion and cation. The requirement for a small, polar anion is indicated by the high solubility of cellulose in the chloride-containing ionic liquids, with reduced solubility in the bromide systems and no solubility in tetrafluoroborate and hexafluorophosphate systems.

The solubility also appears to decrease with increasing the size of the cation such as by increasing the length of the alkyl group, and also by substituting a methyl-function on the C-2 position (an $R^3$ group) of the imidazolium ring. Thus, both charge density and hydrogen bond donating ability in the cation can be important and can be easily and selectively modified by variation in the ionic liquid functionality. Such modification permits simple control of the rheology and composition of the solutions, which is of benefit for subsequent processing of the dissolved cellulose. The presence of water in the ionic liquid was shown to significantly decrease the solubility of cellulose, presumably through competitive hydrogen bonding to the cellulose microfibrils that inhibits solubilization.

Primary studies were conducted with regenerated fibrous cellulose. Additional studies were also carried out on other cellulose samples. Three dried-dissolving pulp samples from production lines were investigated. Sample A, a wood pulp used in cellulose acetate applications, has a 98.7 percent R-18; Sample B, a wood pulp used in lyocell applications, has a 97.5 percent R-18; Sample C, a wood pulp used in rayon applications, [has a 96.8 percent R-18. [The R-18 test is a TAPPI (Technical Association of Pulp and Paper Industry) standardized test that measures the fraction of cellulose resistant to dissolving in 18 percent caustic soda solution.] The degree of polymerization (DP; measure of chain length) for the three pulps are: Sample A; 1056, Sample B; 470, Sample C; 487. All three samples were found to be more readily soluble in [C$_4$mim]Cl than fibrous cellulose.

Fibrous cellulose could be dissolved at greater than 5 percent in [C$_4$mim]Br and [C$_4$mim]SCN ionic liquids, but those dissolutions were more difficult to achieve than when using a [C$_4$mim]Cl system. Under the heating conditions, triethylammonium chloride and tetrabutylammonium chloride decomposed.

In another study, ashless Whatman filter paper was dissolved in [C$_4$mim]Cl ionic liquid using the above-described microwave process. On initial contacting and microwave heating, the filter paper became translucent and was observed to swell as ionic liquid was absorbed into the matrix. On further heating and agitation, the filter paper dissolved completely at 5 percent by weight loading to provide a colorless, clear solution. When the ionic liquid was loaded to 10 weight percent with filter paper, complete dissolution became much more difficult and a viscous solution that contained residual ionic liquid impregnated filter paper was obtained.

All three wood pulp samples were more readily dissolved than the fibrous cellulose sample. We performed tests to prepare a 5 percent solution in [$C_4$mim]Cl (0.5 g in 10 g ionic liquid) using microwave heating in 3 second pulses. On increased loading, very viscous mixtures are produced, the best description would be a paste. Up to about 25 weight percent loading of the fibrous cellulose, the paste could be worked with a spatula and with extended heating and manipulation yielded a clear material. An inhomogeneous, partially opaque mixture was obtained at higher loading.

EXAMPLE 6

Processing Cellulose Solutions

Solutions of cellulose in ionic liquids can be processed simply. Cellulose can be regenerated from the ionic liquid solution by admixing the cellulose-containing ionic liquid with water. Other precipitating solutions can also be used. Illustrative of such solutions are ethanol, acetone, water, and aqueous or neat salt solutions The cellulose can be regenerated in a wide range of macroscopic forms depending on how the contacting of the ionic liquid solution and the regeneration liquid is achieved. Monoliths, fibers and films have been prepared to illustrate the scope for processing of cellulose from ionic liquid by forming into an aqueous phase. Rapid mixing of the ionic liquid solution with an aqueous stream results in precipitation of cellulose as a powdery floc. Alternatively, extruding of the ionic liquid/cellulose solution into a non-solvent (for example) water enables thin fibers and rods to be prepared, as is seen in FIG. 1. The initial extrudate is malleable, and hardens in contact with water as the ionic liquid diffuses from the extrudate into solution.

A cellulose film can be obtained by coating an appropriate surface such as a glass microscope slide with an even layer of the cellulose solution (approximately 1–2 mm thick). The slide was then immersed in a water bath. Initial, regenerated cellulose samples were flexible and apparently very porous. On drying, significant shrinkage occurred to form a hard, resilient film.

A cellulose from an ionic liquid solution can also be molded into various forms. The solution is poured into a mold and a non-solvent added to cause the cellulose to precipitate.

Because the viscosity of the solution and the cellulose concentration can be controlled independently by the choice of a different ionic liquid from a homologous series (e.g. [$C_4$mim]Cl or [$C_6$mim]Cl) or by changing the temperature, processing conditions can be optimized for a particular product preparation. Thus, control of the ionic liquid solution and water contacting methodology permits cellulose to be regenerated from solution with a wide variety of morphologies by simple variation of the processing conditions and ionic liquid.

The use of water as the regenerating solution has potential environmental benefits and cost advantages over current processing methodologies which make use of volatile organic solvents. The ionic liquid can be recovered from aqueous solution and reused by removing the water. This water removal method has been demonstrated on a laboratory scale by evaporating the aqueous/ionic liquid solution to dryness. However, on an industrial scale, other methods for removal of water may prove to be more practical. Illustrative alternatives include reverse osmosis, pervaporation, and salting out of the ionic liquid.

EXAMPLE 6

Physical Properties of Regenerated Cellulose

The regenerated cellulose was characterized by differential scanning calorimetry (DSC), thermogravimetric analysis (TGA), and powder X-ray diffraction (XRD) to determine whether regeneration from the ionic liquid had caused any changes in the molecular morphology of the cellulose. Scanning electron microscopy (SEM) was used to observe the bulk structure of the cellulose materials prepared by regeneration from the ionic liquid (see FIG. 5).

DSC and TG thermograms were collected for cellulose precipitated from the ionic liquid solution, and were compared to the original cellulose material. Samples were placed in a platinum sample holder and heated to 600° C. under a nitrogen atmosphere at 10° C. min$^{-1}$.

Figure 2:
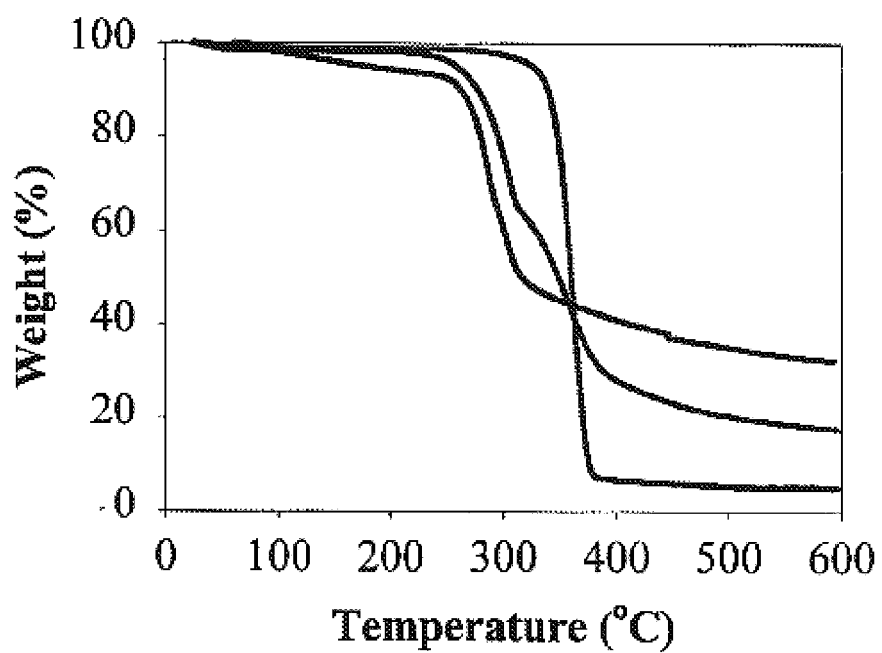
FIG. 2 is a graph that shows a comparison of thermogravimetric analysis (TGA) traces of regenerated cellulose samples (blue, black) with original fibrous cellulose (red)

FIG. 2 shows the TGA curves for the original fibrous cellulose and regenerated form, prepared from [$C_4$mim]Cl. Pure cellulose shows rapid decomposition in a narrow temperature range from 350–360° C. Regeneration from the ionic liquid lowers the onset temperature for decomposition, but results in higher char yields (non-volatile carbonaceous material) on pyrolysis.

Figure 3A:
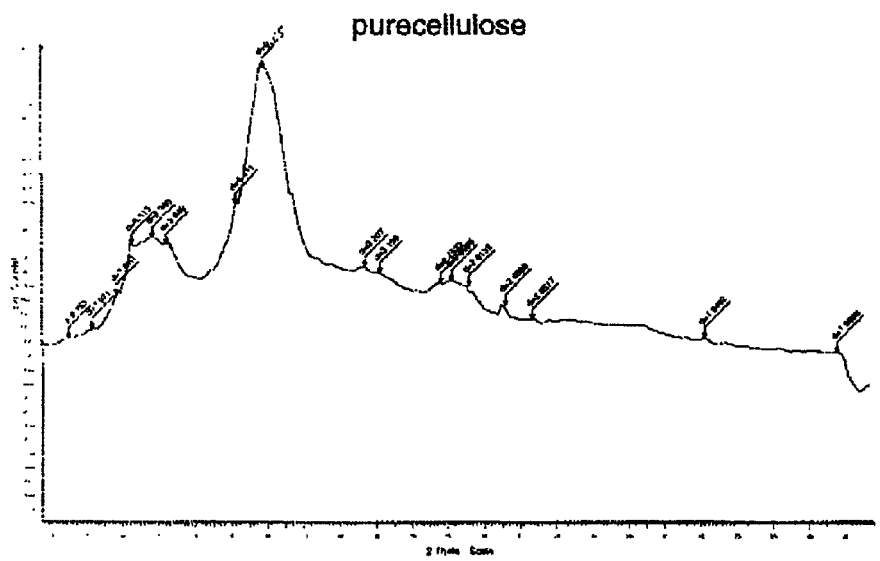
FIG. 3, in two panels as FIGS. 3A and 3B, respectively, show X-ray diffraction (XRD) patterns of original fibrous cellulose (FIG. 3A) and fibrous cellulose regenerated from [$C_4$mim]Cl (FIG. 3B)
Figure 3B:
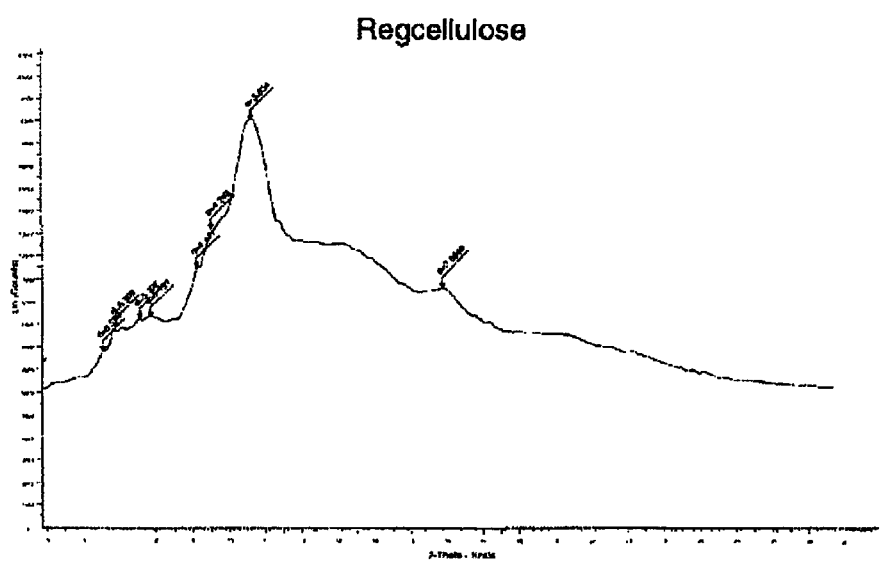
Figure 4A:
FIG. 4, in four panels as FIGS. 4A, 4B, 4C and 4D, are scanning electron micrographs of fibrous cellulose (4A, 4B) and cellulose Sample A (a wood pulp used in cellulose acetate applications; 4C, 4D) before (4A, 4C) and after regeneration from [$C_4$mim]Cl into water (4B, 4D).
Figure 4B:
Figure 4C:
Figure 4D:

For fibrous cellulose reformed from [$C_4$mim]Cl, powder XRD shows only small changes in the morphology. The degree of crystallinity of fibrous cellulose appears to be slightly decreased after dissolution and regeneration from [$C_4$mim]Cl as indicated by the relative intensity and shape of the sharp peak at about 100 (d=4 Å) and the broad underlying diffraction band, shown in FIG. 3.

The crystallinity index of cellulose, $I_c$, can be calculated using the following equation:

$$I_c = 1 - (I_{min}/I_{max})$$

where $I_{min}$ is the intensity minimum between 2=18–19°, and the $I_{max}$ is the intensity of the crystalline peak at the maximum between 2θ=22–23°. This was taken from:

Marson et al., *Journal of Applied Polymer Science*, 1999, 1355–1360.

In a sample that was stored in the ionic liquid for several weeks, then regenerated, the XRD is different, and lacks the characteristic peaks for the cellulose crystalline regions. A single broad band was observed, characteristic of an amorphous material. This may indicate a slow breakdown of the polymer chains with time, as is observed after the swelling of cellulose in liquid ammonia to generate the cellulose III form.

A sample of fibrous cellulose was dissolved in [C4mim]Cl to give a homogeneous 5 weight percent solution. The two samples were then separately regenerated as (i) a floc into water, and (ii) as a rod by extruding into water from a syringe. Both regenerated forms were washed with water, then air dried for 1 week to ensure equilibration of the moisture content with the ambient atmosphere.

The powder XRD traces and crystallinity indices determined for the original fibrous cellulose, and the two regenerated forms are shown the figures below. In these particular studies, the powdery regenerated floc showed an amorphous diffraction pattern with no crystallinity, whereas the extruded-rod form had a crystallinity index that was indistinguishable from the original fibrous material. These results indicate that the degree of crystallinity (and hence, microstructure) of the cellulose can be manipulated during the regeneration process to manufacture materials with microcrystallinity varying from crystalline to amorphous.

The modifications to the bulk structure of regenerated cellulose are shown from scanning electron micrographs, in FIG. 5, of the initial untreated samples and cellulose regenerated from the [$C_4$mim]Cl. Initial samples of fibrous cellulose and dissolving pulp show fibers at 300× magnification in the SEM. After regeneration, in both cases, the cellulose had a completely changed morphology and displayed a rough, but conglomerate texture in which the fibers have fused. SEM data indicate that the cellulose fibrils can be solubilized and regenerated with a relatively homogenous macrostructure.

EXAMPLE 7

Removal of Ionic Liquid from Regenerated Cellulose

A series of studies was conducted to determine whether ionic liquids were trapped or encapsulated within the cellulose matrix during the regeneration process. Using a carbon-14 labeled sample of [$C_4$mim]Cl as the dissolving solvent, a sample of fibrous cellulose was dissolved (1 g of a 2% (wt/wt) solution containing 40 μL of carbon-14 labeled [$C_4$mim] Br), then regenerated as an extruded rod. The radioactivity of the sample was determined, and monitored as the sample was sequentially washed by contacting with known volumes of water.

The cellulose/ionic liquid solution was then diluted with 5 mL of deionized water, and the initial activity of the cellulose/ionic liquid/water solution was measured. After sampling, the aqueous phase was decanted, and an additional 5 mL of deionized water were added. This solution was then well mixed, and the activity again measured. This procedure was repeated 10 times.

The change in activity of the aqueous washing solutions with each wash indicates that effectively all ionic liquid was extracted from the cellulose within 4–5 washings, each with 5-times the initial ionic liquid volume. But measuring the residual activity after the tenth washing, it was determined that approximately 76 μg of ionic liquid per gram of cellulose (76 ppm) remained within the regenerated cellulose.

EXAMPLE 8

Cellulose/Ionic Liquid Solutions Properties

When cellulose is dissolved in [$C_4$mim]Cl at high concentrations (>10 wt %), highly viscous solutions were obtained that were optically anisotropic between crossed polarizing filters and displayed birefringence. Solutions of varying concentration of cellulose in [$C_4$mim]Cl in which birefringence was observed under crossed-polarizers are indicated in the Table below. Birefringence is indicative of a liquid crystalline phase, either nematic or smectic, in which the polymer chains are partially ordered with a bulk orientational director. The formation of liquid crystalline polymer solutions is desirable and can be used to prepare high strength materials that conserve the solution anisotropy in the solid phase yielding enhanced mechanical properties.

| Cellulose Solutions with Liquid Crystalline Properties | |
|---|---|
| Concentration of Cellulose (wt/wt %) | Rotates Plane Polarized Light |
| 5% | NO |
| 10% | NO |
| 15% | YES |
| 20% | YES |
| 25% | YES |

Each of the patents, applications and articles cited herein is incorporated by reference. The use of the article "a" or "an" is intended to include one or more.

From the foregoing it will be observed that numerous modifications and variations can be effectuated without departing from the true spirit and scope of the novel concepts of the invention. It is to be understood that no limitation with respect to the specific embodiment illustrated is intended or should be inferred. The disclosure is intended to cover by the appended claims all such modifications as fall within the scope of the claims.

What is claimed is:

1. A method for dissolving cellulose that comprises admixing cellulose with a molten ionic liquid that is molten at a temperature of about −10 to about 100° C. and in the substantial absence of water or a nitrogen-containing base to form an admixture, wherein said ionic liquid is comprised of cations and anions, and agitating the a mixture until dissolution is complete.

2. The method according to claim 1 wherein said admixture is irradiated with microwave radiation to assist in dissolution.

3. The method according to claim 1 wherein the cations of said ionic liquid are selected from the group consisting of

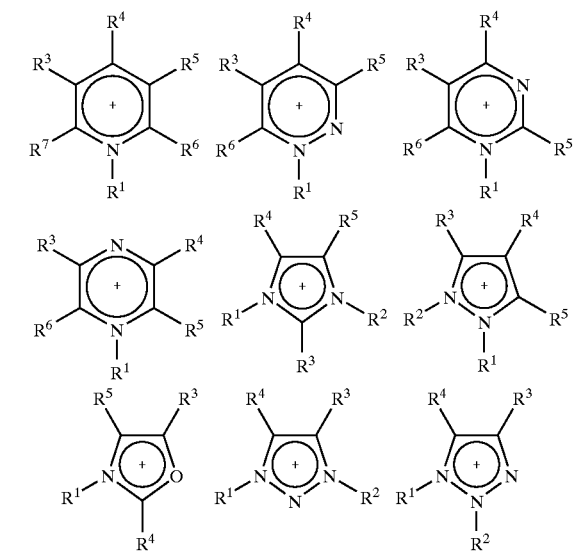

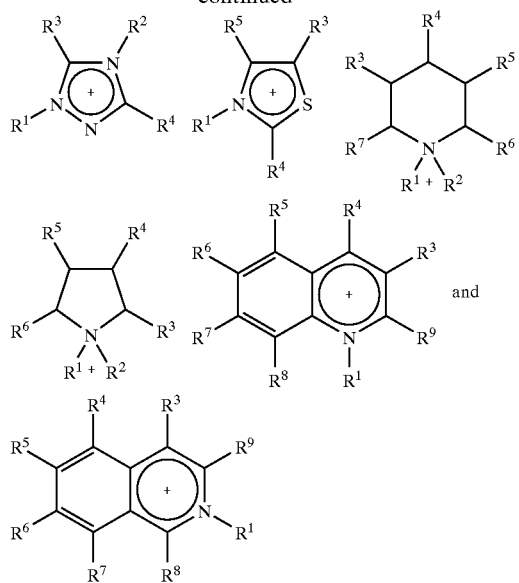

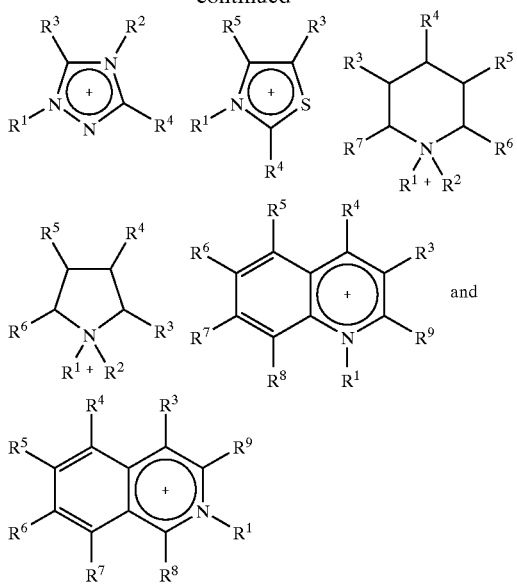

wherein R¹ and R² are independently a $C_1$–$C_6$ alkyl group or a $C_1$–$C_6$ alkoxyalkyl group, and R³, R⁴, R⁵, R⁶, R⁷, R⁸ and R⁹ (R³–R⁹), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_2$–$C_6$ carboxylate.

4. The method according to claim 1 wherein the anions of said ionic liquid are halogen or pseudohalogen.

5. A method for dissolving cellulose that comprises the steps of:
  (a) admixing cellulose with an ionic liquid in the substantial absence of water or nitrogen-containing base to form an admixture, wherein said ionic liquid is molten at a temperature of about −10 to about 100° C. and is comprised of cations and anions, wherein the cations correspond in structure to a formula selected from the group consisting of

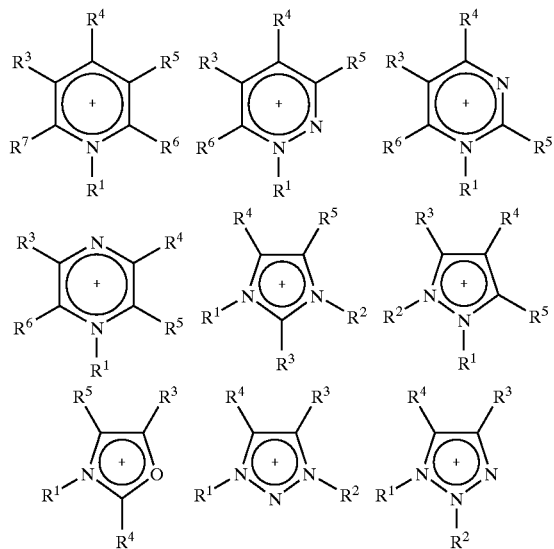

wherein R¹ and R² are independently a $C_1$–$C_6$ alkyl group or a $C_1$–$C_6$ alkoxyalkyl group, and R³, R⁴, R⁵, R⁶, R⁷, R⁸ and R⁹ (R³–R⁹), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_1$–$C_6$ carboxylate;

(b) irradiating said admixture with microwave radiation to assist in dissolution; and
  (c) agitating the admixture until dissolution is complete.

6. The method according to claim 5 wherein said cellulose is fibrous cellulose, wood pulp, linters, cotton balls or paper.

7. The method according to claim 5 wherein said cation contains a single five-membered ring that is free of fusion to other ring structures.

8. The method according to claim 5 wherein R³–R⁹ are hydrido.

9. A method for dissolving cellulose that comprises the steps of:
  (a) admixing cellulose with an ionic liquid comprised of cations and anions in the substantial absence of water to form an admixture, wherein said ionic liquid is molten at a temperature of about −44° C. to about 120° C. wherein said cations contain a single five-membered ring that is free of fusion to other ring structures and said anions are halogen, pseudohalogen, or $C_1$–$C_6$ carboxylate;
  (b) irradiating said admixture with microwave radiation to assist in dissolution; and
  (c) agitating the admixture until dissolution is complete.

10. The method according to claim 9 wherein said cellulose is fibrous cellulose, wood pulp, linters, cotton balls or paper.

11. The method according to claim 9 wherein said cations have a structure that corresponds to a formula selected from the group consisting of

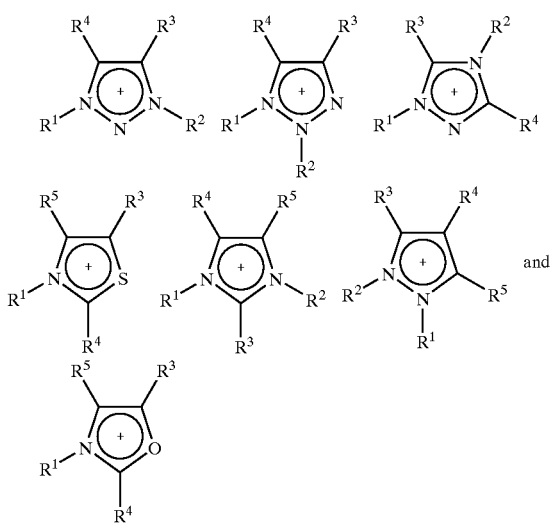

wherein $R^1$ and $R^2$ are independently a $C_1$–$C_6$ alkyl group or a $C_1$–$C_6$ alkoxyalkyl group, and $R^3$, $R^4$, $R^5$ ($R^3$–$R^5$) are independently a hydrido, a $C_1$–$C_6$ alkyl group, a $C_1$–$C_6$ alkoxyalkyl group or a $C_1$–$C_6$ alkoxy group.

12. The method according to claim 11 wherein $R^3$–$R^5$ are hydrido.

13. The method according to claim 11 wherein said cation is a 1,3-di-$C_1$–$C_6$-alkyl imidazolium ion.

14. The method according to claim 13 wherein one of said 1,3-di-$C_1$–$C_6$-alkyl groups is methyl.

15. A method for dissolving cellulose that comprises the steps of:
   (a) admixing cellulose with an ionic liquid comprised of cations and anions in the substantial absence of water to form an admixture, wherein said ionic liquid is molten at a temperature of about −44° C. to about 120° C., wherein the cations are 1,3-di-$C_1$–$C_6$-alkyl imidazolium ions corresponding in structure to Formula A

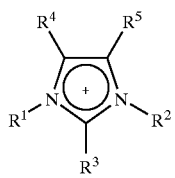

wherein $R^1$ and $R^2$ are independently a $C_1$–$C_6$ alkyl group or a $C_1$–$C_6$ alkoxyalkyl group, and $R^3$, $R^4$, $R^5$ ($R^3$–$R^5$) are independently a hydrido, a $C_1$–$C_6$ alkyl group, a $C_1$–$C_6$ alkoxyalkyl group or a $C_1$–$C_6$ alkoxy group and the anions of the ionic liquid are a halogen or pseudohalogen;
   (b) irradiating said admixture with microwave radiation to assist in dissolution; and
   (c) agitating the admixture until dissolution is complete.

16. The method according to claim 15 wherein said cellulose is fibrous cellulose, wood pulp linters, cotton balls or paper.

17. The method according to claim 15 wherein $R^3$–$R^5$ are hydrido, and $R^1$ and $R^2$ are each a $C_1$–$C_6$ alkyl group.

18. The method according to claim 15 wherein one of said $C_1$–$C_6$-alkyl groups is methyl.

19. The method according to claim 15 wherein said anion is a chloride ion.

20. A method for dissolving cellulose that comprises the steps of:
   (a) admixing cellulose with an ionic liquid comprised of cations and anions in the substantial absence of water to form an admixture, wherein said ionic liquid is molten at a temperature of about −44° C. to about 120° C., and wherein the cations are 1,3-di-$C_1$–$C_6$-alkyl imidazolium ions corresponding in structure to Formula B

wherein $R^1$ is a $C_1$–$C_6$ alkyl group and the anions of the ionic liquid are a halogen or pseudohalogen;
   (b) irradiating said admixture with microwave radiation to assist in dissolution; and
   (c) agitating the admixture until dissolution is complete.

21. The method according to claim 20 wherein said cellulose is fibrous cellulose, wood pulp, linters, cotton balls or paper.

22. The method according to claim 20 wherein said $R^1$ $C_1$–$C_6$ alkyl group is a $C_1$–$C_4$ alkyl group.

23. The method according to claim 20 wherein said anions are chloride ions.

24. A solution comprised of cellulose in a molten ionic liquid solvent that is substantially free of water or a nitrogen-containing base, wherein said ionic liquid is comprised of cations and anions and is molten at a temperature of about −44° C. to about 120° C., and wherein said cations contain a single five-membered ring that is free of fusion to other ring structures and said anions are halogen, pseudohalogen, or $C_1$–$C_6$ carboxylate.

25. The solution according to claim 24 wherein said cellulose is present in an amount of about 5 to about 35 weight percent of the solution.

26. The solution according to claim 24 wherein said cations of said ionic liquid correspond in structure to a formula selected from the group consisting of

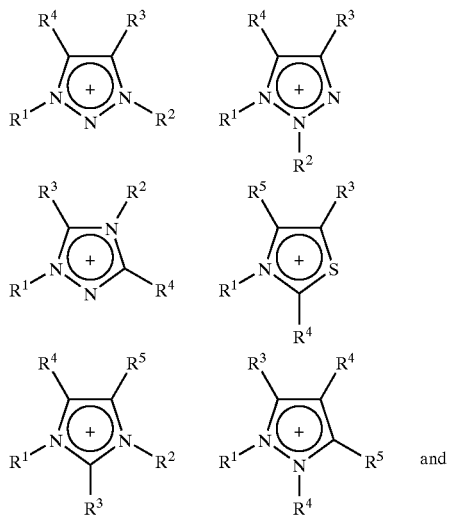

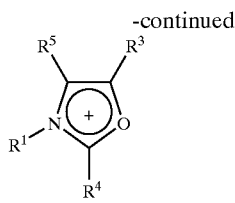

wherein $R^1$ and $R^2$ are independently a $C_1$–$C_6$ alkyl group or a $C_1$–$C_6$ alkoxyalkyl group, and $R^3$, $R^4$, and $R^5$ ($R^3$–$R^5$), when present, are independently a hydrido, a $C_1$–$C_6$ alkyl, a $C_1$–$C_6$ alkoxyalkyl group or $C_1$–$C_6$ alkoxy group, and the anions of the ionic liquid are halogen, pseudohalogen, or $C_1$–$C_6$ carboxylate.

27. The solution according to claim 24 wherein the anions of said ionic liquid are halogen or pseudohalogen.

28. A solution comprise of about 5 to about 35 weight percent cellulose in an ionic liquid solvent that is molten at a temperature of about −10 about 100° C. and is substantially free of water or nitrogen-containing base, wherein said ionic liquid is comprised of cations and anions in which the cations correspond in structure to a formula selected from the group consisting of

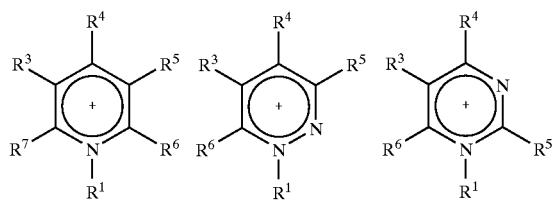

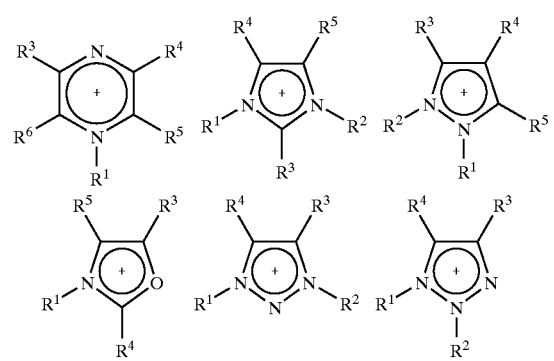

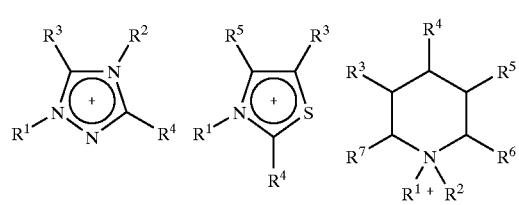

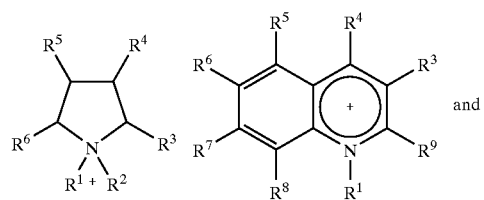

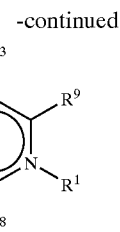

wherein $R^1$ and $R^2$ are independently a $C_1$–$C_6$ alkyl group or a $C_1$–$C_6$ alkoxyalkyl group, and $R^3$, $R^4$, $R^5$, $R^6$, $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_1$–$C_6$ carboxylate.

29. The solution according to claim 28 wherein said cations contain a single five-membered ring that is free of fusion to other ring structures.

30. The solution according to claim 29 wherein said cations have a structure that corresponds to a formula selected from the group consisting of

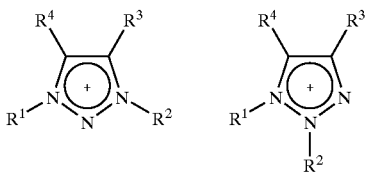

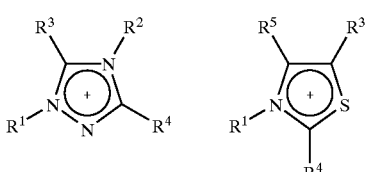

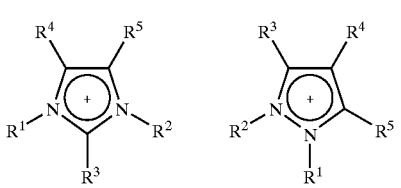

and

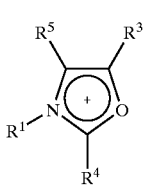

wherein $R^1$ and $R^2$ are independently a $C_1$–$C_6$ alkyl group or a $C_1$–$C_6$ alkoxyalkyl group, and $R^3$, $R^4$, $R^5$ ($R^3$–$R^5$) are independently a hydrido, a $C_1$–$C_6$ alkyl group, a alkoxyalkyl group or a $C_1$–$C_6$ alkoxy group.

31. The solution according to claim 30 wherein said cation is a 1,3-di-$C_1$–$C_6$ alkyl imidazolium ion that corresponds in structure to Formula A

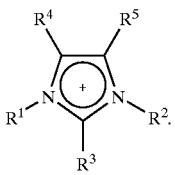

A

32. The solution according to claim 31 wherein one of said 1,3-di-$C_1$–$C_6$ alkyl groups is methyl.

33. The solution according to claim 31 wherein said $R^3$–$R^5$ groups are each hydrido.

34. The solution according to claim 31 wherein said cellulose is present in an amount of about 10 to about 25 weight percent.

35. A solution comprised of about 10 to about 25 weight percent cellulose in an ionic liquid solvent that is molten a temperature of about −10 to about 100° C. and is substantially free of water, wherein said ionic liquid is comprised of cations and anions in which the cations are 1,3-di-$C_1$–$C_6$ alkyl imidazolium ions corresponding in structure to Formula A

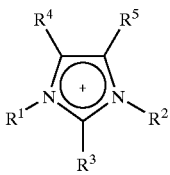

A wherein $R^1$ and $R^2$ are independently a $C_1$–$C_6$ alkyl group or a $C_1$–$C_6$ alkoxyalkyl group, and $R^3$, $R^4$, $R^5$ ($R^3$ $R^5$) are independently a hydrido, a $C_1$–$C_6$ alkyl group, a $C_1$–$C_6$ alkoxyalkyl group or a $C_1$–$C_6$ alkoxy group and the anions of the ionic liquid are a halogen or pseudohalogen.

36. The solution according to claim 35 wherein one of said 1,3-di-$C_1$–$C_6$ alkyl groups is methyl.

37. The solution according to claim 35 wherein said $R^3$–$R^5$ groups are each hydrido.

38. The solution according to claim 37 wherein the other of said $R^1$ is $C_1$–$C_4$-alkyl.

39. The solution according to claim 38 wherein said cations correspond in structure to Formula B

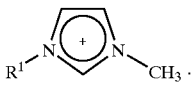

B

40. The solution according to claim 39 wherein said anions are chloride ions.

41. A method for regenerating cellulose that comprises admixing a solution of cellulose in a molten ionic liquid solvent that is substantially free of water or nitrogen-containing base, wherein said ionic liquid is comprised of cations and anions and said molten ionic liquid is either (i) molten at a temperature of about −10° C. to about 100° C. or (ii) is molten at a temperature of about −44° C. to about 120° C. and wherein said cations contain a single five-membered ring that is free of fusion to other ring structures, with a liquid non-solvent for said cellulose that is miscible with said ionic liquid, said admixing causing the cellulose and ionic liquid to form solid and liquid phases, respectively.

42. The method according to claim 41 wherein the cations of said ionic liquid correspond in structure to a formula selected from the group consisting of

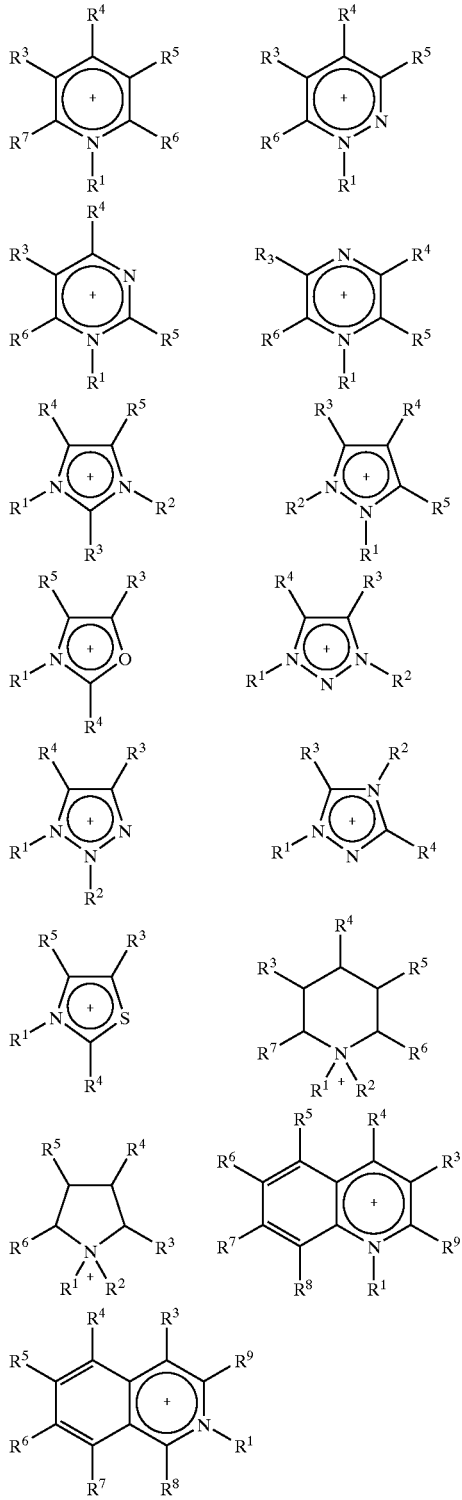

and wherein $R^1$ and $R^2$ are independently a $C_1$–$C_6$ alkyl group or a $C_1$–$C_6$ alkoxyalkyl group, and $R^3$, $R^4$, $R^5$, $R^6$, $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_1$–$C_6$ carboxylate.

43. The method according to claim 41 wherein the anions of said ionic liquid are halogen or pseudohalogen.

44. The method according to claim 41 including the further step of collecting the formed cellulose phase.

45. A method for regenerating cellulose that comprises the steps of:

(a) admixing a solution of cellulose in a molten ionic liquid solvent that is molten at a temperature of less than about 150° C. and is substantially free of water or a nitrogen-containing base, wherein said ionic liquid is comprised of cations and anions, with a liquid non-solvent for said cellulose that is miscible with said ionic liquid, said admixing causing the cellulose and ionic liquid to form solid and liquid phases, respectively, wherein the cations correspond in structure to a formula selected from the group consisting of

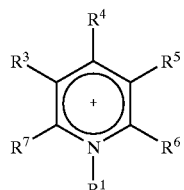
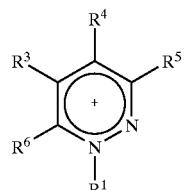
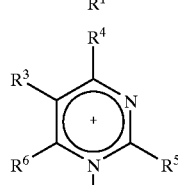
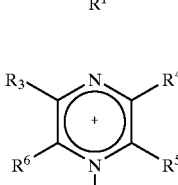
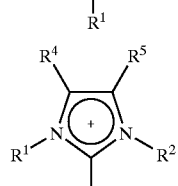
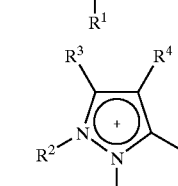
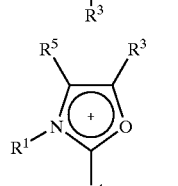
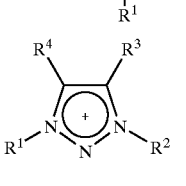
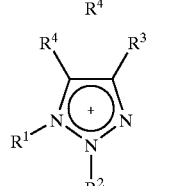
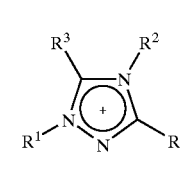
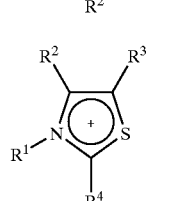
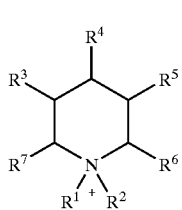

-continued

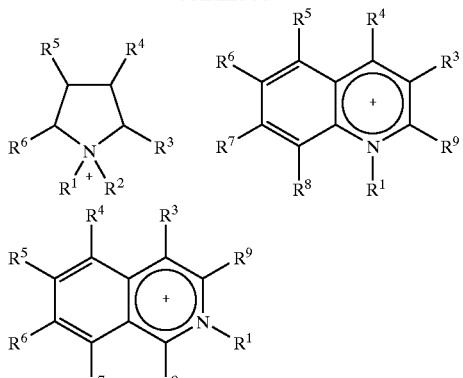

wherein $R^1$ and $R^2$ are independently a $C_1$–$C_6$ alkyl group or a $C_1$–$C_6$ alkoxyalkyl group, and $R^3$, $R^4$, $R^5$, $R^6$ $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_1$–$C_6$ carboxylate and the anions of said ionic liquid are halogen or pseudohalogen; and (b) collecting the formed cellulose phase.

46. The method according to claim 45 wherein said ionic liquid is molten at a temperature of about −44° to about 120° C.

47. The method according to claim 45 wherein said liquid non-solvent for said cellulose that is miscible with said ionic liquid is also miscible with water.

48. A method for regenerating cellulose that comprises the steps of:

(a) admixing a solution of cellulose in a molten ionic liquid solvent that is molten at a temperature of about −44° to about 120° C. and is substantially free of water, herein said ionic liquid is comprised of cations and anions, with a liquid non-solvent for said cellulose that is miscible with said ionic liquid and is also miscible with water, said admixing causing the cellulose and ionic liquid to form solid a d liquid phases, respectively, wherein the cations correspond in structure to a formula selected from the group consisting of

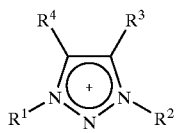
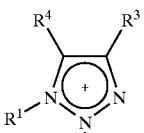
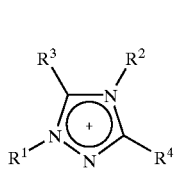
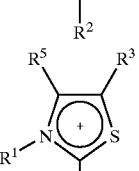
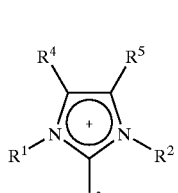
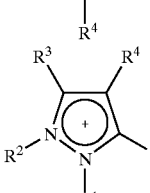

and

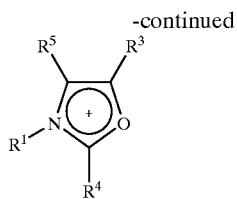

wherein $R^1$ and $R^2$ are independently a $C_1$–$C_6$ alkyl group or a $C_1$–$C_6$ alkoxyalkyl group, and $R^3$, $R^4$, $R^5$ ($R^3$–$R^5$) are independently a hydrido, a $C_1$–$C_6$ alkyl group, a $C_1$–$C_6$ alkoxyalkyl group or a $C_1$–$C_6$ alkoxy group and the anions of the ionic liquid are a halogen or pseudohalogen; and (b) collecting the formed cellulose phase.

49. The method according to claim 48 wherein said cation is a 1,3-di-$C_1$–$C_6$ alkyl imidazolium ion that corresponds in structure to Formula A

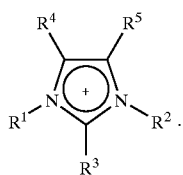

A

50. The method according to claim 49 wherein one of said 1,3-di-$C_1$–$C_6$ alkyl groups is methyl.

51. The method according to claim 50 wherein $R^1$ is $C_1$–$C_4$-alkyl.

52. The method according to claim 51 wherein said $R^3$–$R^5$ groups are each hydrido.

53. The method according to claim 52 wherein said anions are chloride ions.

54. The method according to claim 53 wherein said liquid non-solvent for said cellulose that is miscible with said ionic liquid and is also miscible with water is water, an alcohol or ketone.

55. The method according to claim 54 wherein said admixing step is carried out by extruding said cellulose solution through a die and into said non-solvent.

56. The method according to claim 51 wherein said cations correspond in structure to Formula B

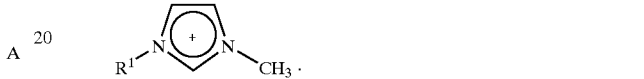

B

57. The method according to claim 56 wherein said cellulose is initially present in said solution in an amount of about 10 to about 25 weight percent.

58. The method according to claim 57 wherein said liquid non-solvent is water.

* * * * *